United States Patent
Bath

[19]

[11] Patent Number: 5,843,071
[45] Date of Patent: Dec. 1, 1998

[54] METHOD AND APPARATUS FOR ABLATING AND REMOVING CATARACT LENSES

[76] Inventor: Patricia E. Bath, 4554 Circle View Blvd., Los Angeles, Calif. 90024

[21] Appl. No.: 441,213

[22] Filed: May 15, 1995

Related U.S. Application Data

[62] Division of Ser. No. 717,794, Jun. 19, 1991, abandoned, which is a continuation of Ser. No. 159,931, Feb. 24, 1998, abandoned, which is a division of Ser. No. 943,098, Dec. 18, 1986, Pat. No. 4,744,360.

[51] Int. Cl.⁶ .................................................. A61N 5/06
[52] U.S. Cl. ................................ 606/6; 606/3; 606/10; 606/15
[58] Field of Search ........................... 606/2–18

[56] References Cited

U.S. PATENT DOCUMENTS

| | | |
|---|---|---|
| 3,821,510 | 6/1974 | Muncheryan . |
| 3,843,865 | 10/1974 | Nath . |
| 3,858,577 | 1/1975 | Bass et al. . |
| 3,865,113 | 2/1975 | Sharon et al. . |
| 3,982,541 | 9/1976 | L'Esperance .............................. 606/3 |
| 4,122,853 | 10/1978 | Smith . |
| 4,273,109 | 6/1981 | Enderby . |
| 4,517,974 | 5/1985 | Tanner . |
| 4,537,193 | 8/1985 | Tanner . |
| 4,564,011 | 1/1986 | Goldman . |
| 4,583,539 | 4/1986 | Karlin et al. . |
| 4,646,737 | 3/1987 | Hassein et al. .............................. 606/7 |
| 4,686,979 | 8/1987 | Gruen et al. . |
| 4,694,828 | 9/1987 | Eichenbaum ................................ 606/6 |
| 4,702,245 | 10/1987 | Schröder et al. ............................. 606/4 |
| 4,846,172 | 7/1989 | Berlin .......................................... 606/4 |

FOREIGN PATENT DOCUMENTS

| | | |
|---|---|---|
| 0 033 958 | 8/1981 | European Pat. Off. . |

*Primary Examiner*—David M. Shay

[57] ABSTRACT

A method and apparatus for removing cataracts in which a flexible line preferably 1 mm or less in diameter is inserted through an incision into the anterior chamber until its end is adjacent the cataract. Coherent radiation, preferably at a frequency between 193 and 351 nm, is coupled to the cataract by an optical fiber in the line. An irrigation sleeve provided about the fiber and an aspiration sleeve extending partially around the irrigation sleeve conduct irrigating liquid to and remove ablated material from the anterior chamber and form with the optical fiber the flexible line.

19 Claims, 1 Drawing Sheet

METHOD AND APPARATUS FOR ABLATING AND REMOVING CATARACT LENSES

This is a divisional of application Ser. No. 07/717,794 filed on Jun. 19, 1991, now abandoned, which is a continuation of Ser. No. 07/159,931, Feb. 24, 1988, now abandoned, which is a division of Ser. No. 06/943,098, filed Dec. 18, 1986, now U.S. Pat. No. 4,744,360.

BACKGROUND AND SUMMARY OF THE INVENTION

The invention relates to a method and apparatus for coupling laser radiation to a cataract lens in the eye to ablate the same.

Every eye is divided into an anterior and posterior chamber separated by a normally transparent lens which focuses light onto the retina at the back of the posterior chamber. When the lens becomes cloudy for any of a variety of reasons sight is impaired and the cloudy lens must be removed. Following removal of the lens, an inter ocular lens (IOL) implant can be placed in the posterior chamber or thick glasses or contact lenses used to focus the light.

A number of techniques are now in use for this common surgical procedure. An incision can be made in the eye and a sharp instrument inserted to cut and then aspirate by vacuum the cloudy cataract tissue. More recently, a small incision—typically 3 mm—can be made in the eye surface and an ultrasonic probe inserted to a position adjacent the lens. The ultrasonic energy then disintegrates the lens material which can likewise be removed by aspiration.

Laser radiation is now used widely in various surgical techniques particularly those involving the eye. For example, the patent to Krasnov, 3,971,382, describes a technique in which laser radiation is focused onto the anterior capsule of the lens to form a hole through which the cataract substance can be drawn from the lens capsule.

Optical fibers are also commonly used for medical and other applications to transmit coherent radiation from a laser to some location in the body where material is to be coagulated or disintegrated. U.S. Pat. application Ser. No. 702,569, filed Feb. 19, 1985, describes a micro instrument with an optical fiber. The optical fiber can be inserted into the eye for the removal of abnormal tissue such as tumors. Radiation with a wavelength between 200 and 400 nm is said to be appropriate.

The present invention relates to a method and apparatus in which coherent radiation is transmitted by a flexible line containing an optical fiber is inserted through a limbel incision, preferably 1 mm or less, in the eye surface and then through a 1 mm or less anterior capsulatomy into the lens nucleus. The optical fiber is then positioned within the crystalline lens.

Coherent radiation disintegrates the crystalline material into extremely small particles less than 0.1 mm in diameter. These nuclear particles and cortex can then be irrigated and aspirated from the capsular bag, which is left intact, except for the 1 mm anterior capsulatomy, via an aspiration sleeve which is formed about and extending along the optical fiber. At the same time irrigating liquid is supplied via an irrigation sleeve likewise formed about and extending along the optical fiber.

Since the particles produced by this ablation are so small, the device can be made to be extremely small and therefore, the incision likewise can be made much smaller than with other techniques such as ultrasonic. Utilizing an optical fiber further permits the energy to be more efficiently and effectively focused onto the lens to be removed.

Radiation in the, range of 193 to 351 nm has proved to be satisfactory. In particular, 308 nm was found to be the most effective experimental wavelength. However, the invention is also effective at other wavelengths, for example, between 193 nm and 3000 nm.

DETAILED DESCRIPTION OF THE PREFERRED EMBODIMENT

Figure 1:
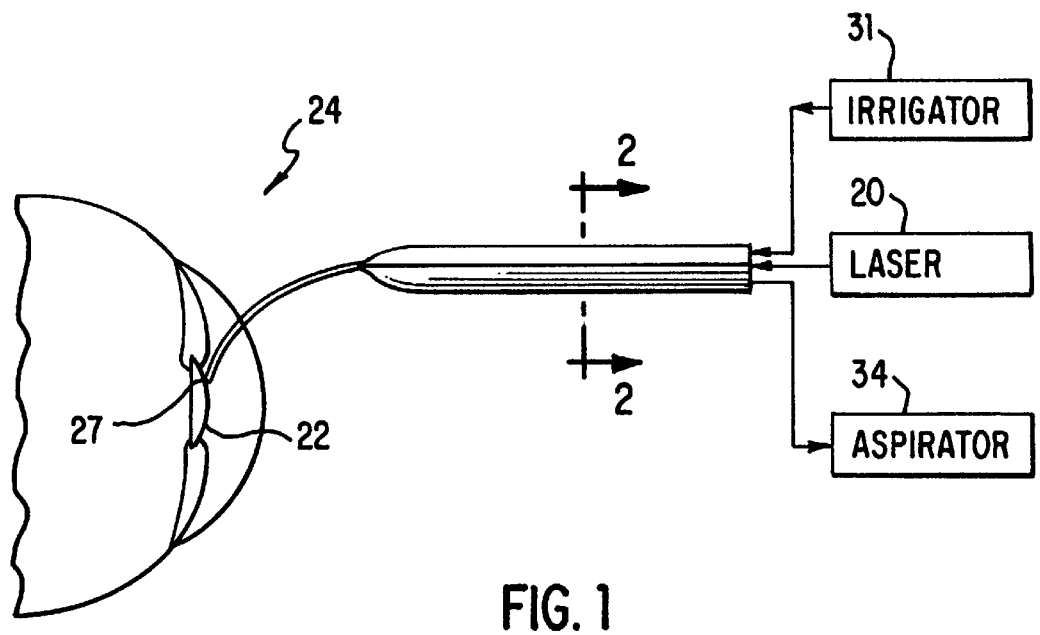
FIG. 1 shows a schematic view of the present invention being used for ablating a cataract lens.
Figure 2:
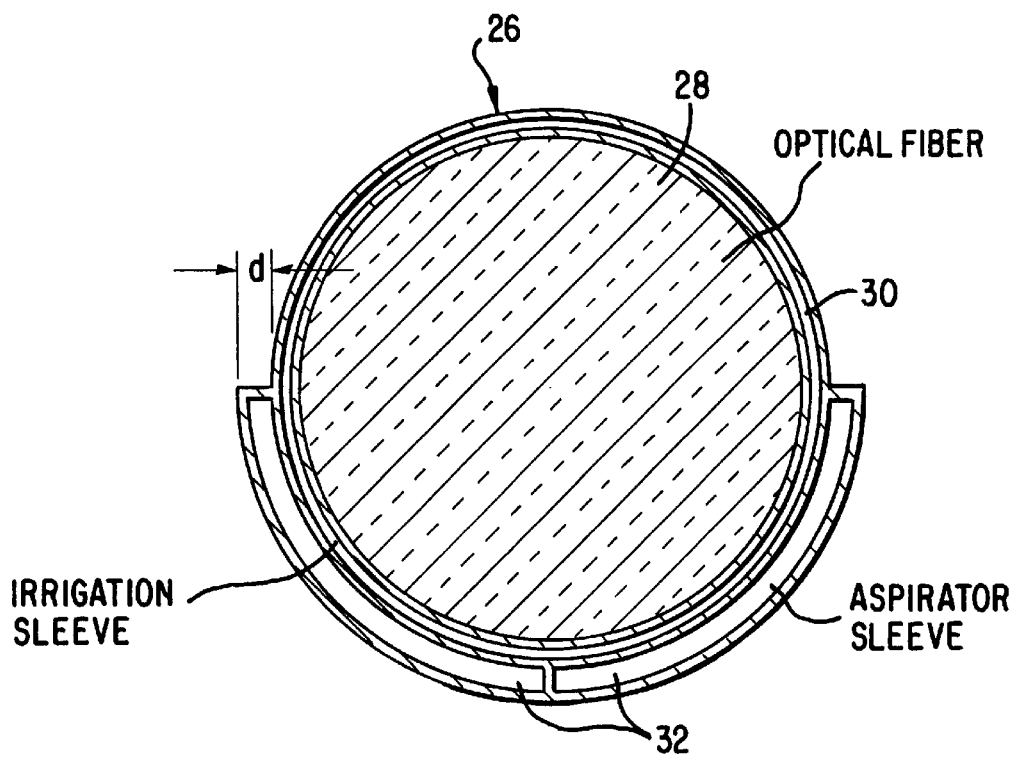
FIG. 2 shows a cross-section of the flexible line of FIG. 1 along the lines 2—2.

Reference is now made to FIGS. 1 and 2 which illustrate a preferred embodiment of the present invention. First, a flexible line 26 is introduced into the interior of the lens nucleus through a 1 mm limbel incision and a 1 mm anterior capsulatomy. Pulsed excimer coherent radiation from a suitable and conventional laser 20 at a suitable energy is coupled to the interior aspect of a cataract lens 22 in a human or animal eye 24 by a flexible line 26 having an unshielded distal end face 27 until the desired amount of ablation occurs.

As can be best seen in FIG. 2, flexible line 26 is formed of a conventional optical fiber suitable for medical applications, for example, quartz silica. In that the distal end face 27 of the line 26 is unshielded, the distal end face of the optical fiber within the line is unshielded. The flexible line 26, formed of the conventional optical fiber is then directed successively to the inferior, central and superior areas of the lens nucleus and phakoablation again performed at each area. An irrigation sleeve 30 surrounds the optical fiber and is connected to a suitable irrigation device 31 for supplying irrigating liquid to the eye during surgery at a suitable pressure. Aspiration sleeve 32 extends partially around the irrigation sleeve and is coupled to a conventional aspirator 34 for removing by an appropriate suction the minute particles of cataract tissues which are produced in response to incidence of the coherent radiation.

The wavelength of the radiation is preferably in the range as set forth above. Since the particles are so small, the width d of the aspiration sleeve can be 0.3 mm or less. The optical fiber can be made to be no more than 600 microns in diameter and the aspiration sleeve similarly no more than 0.1 mm so that the entire flexible tube 33 can be made of a diameter no greater than 1 mm, permitting the size of the incisions to be minimized.

EXAMPLE

A Lambda Physik 102 Xenon Chloride Excimer laser operating at 308 nm was utilized for these experiments. The laser had unstable resonator optics and rectilinear output aperture producing a 2.2×0.7 beam. The maximum output of the laser was 250 mj. The laser output travelled through a 7 mm hole and was then focused by a quartz lens and optical delivery system which transmitted the optical radiation to the optical fiber (400 mm focal length). The pulse length was 17 nanoseconds and the maximum rep rate was 100 Hertz. By moving the lens, a variation in light flux could be produced. Prior to each irradiation event the pulse energy was measured with a Genetic joulemeter.

Prior to performing ablation the thresholds for ablation of lens nucleus and cortex and bovine lenses was determined.

The target consisted of whole bovine lenses or human lenses with intact lens capsules. Bovine lenses were obtained from freshly enucleated globes using standard microsurgical intracapsular technique. The bovine lenses measured 1 cm in sagittal section, i.e., distance from anterior capsule to posterior capsule. Lenses were tested within 4–8 hours of enucleation.

Human lenses were obtained from freshly enucleated cadaver eyes, preserved by standard moist chamber storage. After excision of the cornea, lenses were delivered using intracapsular microsurgical technique and tested within 12–36 hours post mortem.

Whole lenses were mounted in a 16 mm fixation ring which had a 5 mm aperture. Two methods were utilized to determine the ablation rates. The first method was used for the determination of the ablation rate for the cortex. The entire lens was mounted in the fixation ring and holes were drilled at different energy values, a maximum of 2 mm in the lens. This is essentially equivalent to insertion of an optical fiber during surgery as described above.

For the case of cortex, ablation was essentially absent at energy densities below 7 mj/mm$^2$. In the case of bovine nucleus, the ablation threshold was approximately 10 mj/mm$^2$.

At an energy density of 22 mj/mm$^2$, the ablation rates for bovine cortex and nucleus were 6 microns/pulse and 13 microns/pulse respectively.

At an energy density of 53 mj/mm$^2$, the ablation rates for bovine cortex and nucleus were 42 microns/pulse and 23 microns/pulse, respectively. These differences were statistically significant at the 0.05 level.

The ablation threshold was determined to be approximately 3 mj/mm$^2$. At an energy density of 22 mj/mm$^2$ the ablation rate was approximately 10 microns/pulse. And at energy density of 40 mj/m$^2$ the ablation rate was approximately 40 microns/pulse.

Many changes and modifications of the above described embodiment of the invention can be carried out without departing from the scope of the invention. Accordingly, that scope is intended to be limited only by the scope of the appended claims.

What is claimed is:

1. A method for surgically removing a cataract from the anterior chamber of a mammal's eye, by using a laser, which laser applies pulse energy to the cataract, wherein the cataract is in a cataractous crystalline lens that includes a lens nucleus of crystalline material in which the cataract is formed covered by a cortex, the cataractous crystalline lens being disposed within a capsular bag in the anterior chamber of the eye, the method comprising:

a) making incisions into the anterior chamber and capsular bag;
   b) passing through the incisions an end of a line including an optical fiber, the optical fiber having an unshielded distal end, the optical fiber having the laser optically coupled thereto;
   c) positioning the end of the line adjacent the cataract so that the unshielded distal end of the optical fiber is adjacent the cataractous crystalline lens;
   d) energizing the optical fiber with short pulses to a predetermined threshold level sufficient to ablate the crystalline material of the lens nucleus into particles, while the lens nucleus remains in position; and
   e) while energizing the optical fiber, irrigating with a liquid the lens being ablated and aspirating the liquid with the particles entrained therein to remove the crystalline material and thus the cataract from the eye by applying suction to the liquid.

2. The method of claim 1, wherein the optical fiber is energized with coherent radiation in the range of 193 nm to 3000 nm.

3. The method of claim 1, wherein the optical fiber is a flexible optical fiber.

4. The method of claim 1, wherein the lens nucleus has inferior, central and superior areas and wherein the optical fiber is directed successively to the inferior, central and superior areas.

5. The method of claim 1, wherein the optical fiber is solid.

6. The method of claim 1, wherein the optical fiber is a single strand.

7. The method of claim 1 wherein the short pulses are in the nanosecond range.

8. The method of claim 1, wherein irrigating and aspirating the lens being ablated occurs by conveying liquid to and away from the lens along an axis of the lens which is coextensive with the longitudinal axis of the optical fiber.

9. The method of claim 8, wherein the liquid conveyed to the lens for irrigating the lens is conveyed next to the optical fiber in an annular tube extending coaxially with and in engagement with the optical fiber.

10. The method of claim 9, wherein the liquid carried away from the lens for aspirating the lens is conveyed in a tube positioned next to the annular tube.

11. The method of claim 1 further including measuring the pulse energy of the laser just prior to energizing the optical fiber.

12. The method of claim 11, wherein the optical fiber is energized with coherent radiation in the range of 193 nm to 3000 nm.

13. The method of claim 12, wherein the optical fiber is positioned within the cataractous crystalline lens.

14. The method of claim 12, wherein irrigating and aspirating the lens being ablated occurs by conveying liquid to and away from the lens along an axis of the line which is coextensive with the longitudinal axis of the optical fiber.

15. The method of claim 14, wherein the liquid conveyed to the lens for irrigating the lens is conveyed next to the optical fiber in an annular tube extending coaxially with and in engagement with the optical fiber.

16. The method of claim 15, wherein the liquid carried away from the lens while aspirating the lens is conveyed in a tube positioned next to the annular tube.

17. The method of claim 16, wherein the lens nucleus has inferior, central and superior areas and wherein the optical fiber is directed successively to the inferior, central and superior areas.

18. The method of claim 17, wherein the optical fiber is solid.

19. The method of claim 17, wherein the optical fiber is a single strand.

* * * * *